United States Patent
Learmonth

(10) Patent No.: US 7,189,846 B2
(45) Date of Patent: Mar. 13, 2007

(54) METHOD FOR RACEMIZATION OF (S)-(+)- AND (R)-(−)-10,11-DIHYDRO-10-HYDROXY-5H-DIBENZ[B,F]AZEPINE-5-CARBOXAMIDE AND OPTICALLY ENRICHED MIXTURES THEREOF

(75) Inventor: David Alexander Learmonth, Alfena (PT)

(73) Assignee: Portela & C.A., S.A., Mamedo Do Coronado (PT)

( * ) Notice: Subject to any disclaimer, the term of this patent is extended or adjusted under 35 U.S.C. 154(b) by 416 days.

(21) Appl. No.: 10/842,726

(22) Filed: May 10, 2004

(65) Prior Publication Data

US 2004/0266754 A1    Dec. 30, 2004

(30) Foreign Application Priority Data

May 12, 2003    (GB) ................................. 0310856.0

(51) Int. Cl.
*C07D 223/18*    (2006.01)
(52) U.S. Cl. ..................................................... 540/589
(58) Field of Classification Search ................. 540/589
See application file for complete search history.

(56) References Cited

FOREIGN PATENT DOCUMENTS

| GB | 1 495 176 | 12/1977 |
|----|-----------|---------|
| JP | 56073066 | 6/1981 |
| WO | WO 02/092572 | 11/2002 |

OTHER PUBLICATIONS

Great Britain Search Report, GB 0310856.0; Sep. 23, 2003; 3 pages.
Schutz, H. et al.; *The metabolism of C-oxcarbazepine in* man; Xenobiotica; vol. 16; 1986; pp. 769-778.
Benes, J. et al.; *Anticonvulsant and Sodium Channel-Blocking Properties of Novel 10,11-Dihydro-5H-dibenz'b,f]azepine-5-carboxamide Derivatives*; J. Med. Chem.; vol. 42; 1999; pp. 2582-2587.

*Primary Examiner*—Brenda Coleman
(74) *Attorney, Agent, or Firm*—Conley Rose, P.C.; Rodney B. Carroll

(57) ABSTRACT

A high-yielding method and a useful intermediate, 10-chloro-10,11-dihydro-5H-dibenz/b,f/azepine-5-carboxamide (VII) is disclosed. Also disclosed are methods for the racemization of optically pure or optically enriched mixtures of (S)-(+)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II) to racemic (±)-10,11-dihydro-10-hydroxy-5H-dibenz/b,f/azepine-5-carboxamide (III).

35 Claims, No Drawings

METHOD FOR RACEMIZATION OF (S)-(+)- AND (R)-(−)-10,11-DIHYDRO-10-HYDROXY-5H-DIBENZ[B,F]AZEPINE-5-CARBOXAMIDE AND OPTICALLY ENRICHED MIXTURES THEREOF

CROSS-REFERENCE TO RELATED APPLICATIONS

This application is claiming priority of United Kingdom patent application number 0310856.0, filed May 12, 2003, entitled "Method For Racemisation Of (S)-(+)- And (R)-(−)-10,11-Dihydro-10-Hydroxy-5h-Dibenz/B,F/Azepine-5-Carboxamide And Optically Enriched Mixtures Thereof," which is incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention relates to a method for the racemisation of optically pure or optically enriched mixtures of (S)-(+)-10,11-dihydro-10-hydroxy-5H-dibenz/b,f/azepine-5-carboxamide and (R)-(−)-10,11-dihydro-10-hydroxy-5H-dibenz/b,f/azepine-5-carboxamide (compounds of formulas (I) and (II).

BACKGROUND OF THE INVENTION

Racemic (±)-10,11-dihydro-10-hydroxy-5H-dibenz/b,f/azepine-5-carboxamide of formula (III), is a known substance which has been shown to possess anti-convulsant activity (Schutz, H. et al., Xenobiotica, 16, 769–778 (1986)), and was found to be the principal metabolite of the established anti-epileptic drug oxcarbazepine (formula IV). In addition to its anti-convulsant activity, racemic alcohol (III) can be readily synthesised in high yield by reduction of oxcarbazepine (IV), and thus serves as a useful intermediate for the preparation of optically pure (S)-(−)-10-acetoxy-10,11-dihydro-5H-dibenz/b,f/azepine-5-carboxamide (formula V) and (R)-(+)-10-acetoxy-10,11-dihydro-5H-dibenz/b,f/azepine-5-carboxamide (formula VI), two more recently disclosed, single-enantiomer anti-epileptic drugs demonstrating improved biological properties (Benes, J. et al., J. Med. Chem., 42, 2582–2587 (1999)). The (S)-(−)-enantiomer (V) in particular has been shown to display a very favourable anti-convulsant profile.

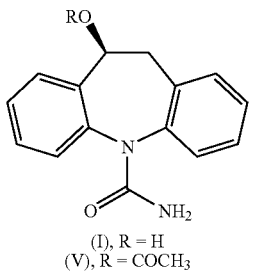

(I), R = H
(V), R = COCH₃

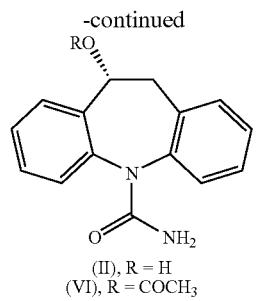

(II), R = H
(VI), R = COCH₃

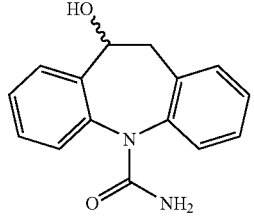

(III)

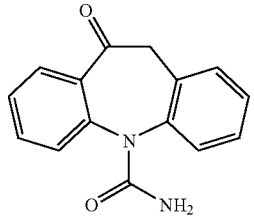

(IV)

A key step in the synthesis of either of the optically pure individual acetate esters (V) or (VI) involves the resolution of racemic (±)-10,11-dihydro-10-hydroxy-5H-dibenz/b,f/azepine-5-carboxamide (III) into its individual, optically pure stereoisomers, (S)-(+)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II), which are the principal intermediates for synthesis of the optically pure acetates (V) and (VI). An improved method for this resolution was recently disclosed involving the efficient separation of diastereoisomeric tartrate half-esters of racemic (±)-10,11-dihydro-10-hydroxy-5H-dibenz/b,f/azepine-5-carboxamide (III) (Learmonth, D., PCT/GB02/02176).

As mentioned above, racemic (±)-10,11-dihydro-10-hydroxy-5H-dibenz/b,f/azepine-5-carboxamide (III) can be easily prepared by simple chemical reduction of the benzylic ketone group of oxcarbazepine (IV), by the use of, for example, metal hydrides in alcoholic medium. However, oxcarbazepine (IV) is an extremely expensive substance, and despite the very efficient resolution procedure (around 98% yield based on a single diastereoisomer), it should be noted that development of say only the (S)-(−)-acetate (V) would mean the loss of approximately 50% of very expensive material. It would thus be highly desirable to have a method of recycling this unwanted, but very expensive (R)-(−)-10,11-dihydro-10-hydroxy-5H-dibenz/b,f/azepine-5-carboxamide (II) which can be recovered from the resolution mixture. This recycling could be envisaged to involve a racemisation procedure, whereby the recovered but unwanted optically enriched (R)-(−)-10,11-dihydro-10-hydroxy-5H-dibenz/b,f/azepine-5-carboxamide enantiomer (II) is converted into racemic (±)-10,11-dihydro-10-hydroxy-5H-dibenz/b,f/azepine-5-carboxamide (III) for re-introduction into the resolution cycle. The racemisation procedure should preferably involve the use of cheap, readily available solvents and reagents, and be operationally simple while affording good yields of pure, completely racemised product. However, in the case of alcohols (I) and (II), racemisation under standard acidic or basic conditions is unusually complicated, principally due to the very facile elimination of water from the molecules of (I) and (II), which leads exclusively to a dehydrated olefinic product of negligible interest for the synthesis of either (V) or (VI).

SUMMARY OF THE INVENTION

It has now been surprisingly found however that racemisation can be readily achieved via a straightforward process, which involves the reaction of optically enriched (enantiomeric excesses in the range from 1 to 99.5%) (R)-(−)-10,11-dihydro-10-hydroxy-5H-dibenz/b,f/azepine-5-carboxamide (II) or (S)-(+)-10,11-dihydro-10-hydroxy-5H-dibenz/b,f/azepine-5-carboxamide (I) with a standard chlorinating agent under suitable substitution conditions which furnishes an intermediate benzylic chloride, 10-chloro-10,11-dihydro-5H-dibenz/b,f/azepine-5-carboxamide (formula VII), which is sufficiently stable and can be easily isolated and, if preferred, purified by standard techniques or be used directly without isolation and purification. This 10-chloro-10,11-dihydro-5H-dibenz/b,f/azepine-5-carboxamide (VII) very conveniently undergoes hydrolysis under simple reaction conditions to provide racemic (±)-10,11-dihydro-10-hydroxy-5H-dibenz/b,f/azepine-5-carboxamide (III) in both high yield and very good purity giving the method of the present invention according to the following synthetic scheme:

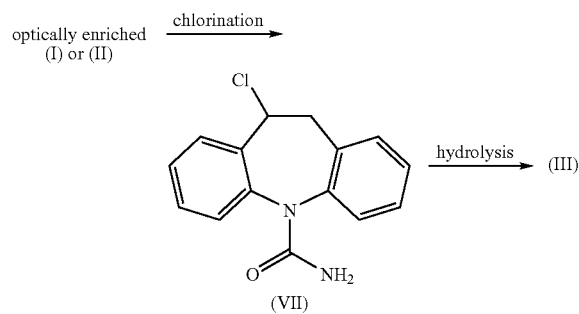

DETAILED DESCRIPTION OF THE INVENTION

According to the present invention, the benzylic alcohol functionality of optically pure or enriched (R)-(−)-10,11-dihydro-10-hydroxy-5H-dibenz/b,f/azepine-5-carboxamide (II) or (S)-(+)-10,11-dihydro-10-hydroxy-5H-dibenz/b,f/azepine-5-carboxamide (I) undergoes substitution by chlorine via reaction with a suitable chlorinating reagent, such as, for example, inorganic or organic acid halides including thionyl chloride, oxalyl chloride, sulfuryl chloride, phosphorus pentachloride, phosphorus trichloride, phosphorus oxychloride and the like. The chlorinating reagent can be used in a 1.02–2 molar ratio with respect to the optically enriched alcohol (I) or (II), preferably in the range 1.05–1.2. The reaction is carried out in a solvent, which is inert under the reaction conditions, such as, for example, dichloromethane, chloroform, carbon tetrachloride, chlorobenzene and the like. The reaction can be carried out over a wide range of temperatures, from −78° C. to the boiling point of the solvent used, preferably in the range 0° C.–25° C. The compound of formula (VII) can be easily isolated from the reaction mixture by procedures familiar to those skilled in the art and if preferred, can be further purified by slurrying or recrystallisation from suitable solvents, such as, for example, esters including ethyl acetate or ketones including acetone and methyl ethyl ketone.

According to the present invention, hydrolysis can be carried out by stirring the intermediate benzylic chloro derivative of formula (VII) in neat water. The reaction can be run over a wide range of temperatures, from 5° C.–100° C., preferably 15° C.–30° C. Once the reaction is complete, the product of racemisation (III) can be conveniently recovered in good yield and high purity by filtration or centrifugation. The product of racemisation (III) can be rapidly analysed by chiral HPLC analysis and is found to be a strictly racemic (1:1) mixture of (S)-(+)-10,11-dihydro-10-hydroxy-5H-dibenz/b,f/azepine-5-carboxamide and (R)-(−)-10,11-dihydro-10-hydroxy-5H-dibenz/b,f/azepine-5-carboxamide, i.e. an equimolar mixture of the compounds of formulas (I) and (II). If preferred, the crude racemic product of formula (III) can be further purified by slurrying or recrystallisation from a suitable solvent, such as, for example esters including ethyl acetate, ketones including acetone and methyl ethyl ketone or lower aliphatic alcohols such as methanol, ethanol and isopropanol.

Alternatively, if preferred, the reaction can be run in the presence of a solubilising, water-miscible solvent such as, for example, dioxane, tetrahydrofuran, lower aliphatic alcohols including methanol, ethanol and isopropanol, N-methyl-2-pyrrolidinone, high molecular weight polyethyleneglycols, acetone, acetonitrile, dimethylformamide and the like. The volume ratio of organic solvent to water lies in the range 1:0.5 to 1:50, and the reaction can be run over a wide range of temperatures, from 5° C.–100° C., preferably 20° C.–60° C. Once the reaction is complete, the racemic product can be isolated by standard procedures familiar to those skilled in the art, and further purified if preferred, and analysed by chiral HPLC as described above.

According to another aspect of the invention, there is provided a method for the preparation of a compound of the general formula (VIII):

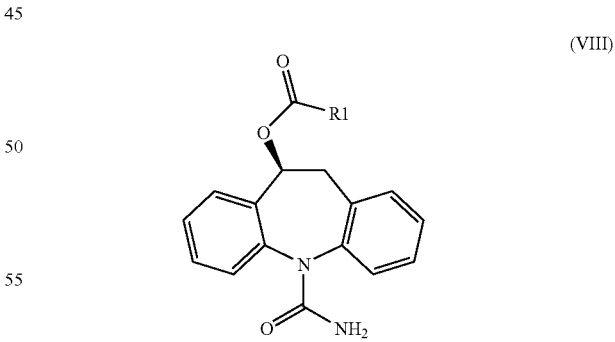

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming racemic (±)-10,11-dihydro-10-hydroxy-5H-dibenz/b,f/azepine-5-carboxamide from optically pure or optically enriched (R)-(−)-10,11-dihydro-10-hydroxy-5H-dibenz/b,f/azepine-5-carboxamide (II) by a process as described above, then treating the racemic (±)-10,11-dihydro-10-hydroxy-5H-dibenz/b,f/azepine-5-carboxamide to produce the compound of formula (VIII).

According to another aspect of the invention, there is provided a method for the preparation of a compound of the general formula (IX):

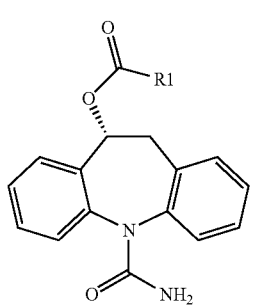

(IX)

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming racemic (±)-10,11-dihydro-10-hydroxy-5H-dibenz/b,f/azepine-5-carboxamide from optically pure or optically enriched (S)-(+)-10,11-dihydro-10-hydroxy-5H-dibenz/b,f/azepine-5-carboxamide (II) by a process as described above, then treating the racemic (±)-10,11-dihydro-10-hydroxy-5H-dibenz/b,f/azepine-5-carboxamide to produce the compound of formula (IX).

Resolution of the recovered racemic (±)-10,11-dihydro-10-hydroxy-5H-dibenz/b,f/azepine-5-carboxamide (III) into its optically pure stereoisomers (S)-(±)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II) is possible as described in more detail in our application no. PCT/GB02/02176. The compounds of formulas (VIII) and (IX) are described in more detail in our U.S. Pat. No. 5,753,646, the contents of which are incorporated herein by reference. The method can be used to produce any of the compounds disclosed in U.S. Pat. No. 5,753,646. For example, to produce (S)-(−)-10-acetoxy-10,11-dihydro-5H-dibenz/b,f/azepine-5-carboxamide (V) it is possible to add acetyl chloride (or acetic anhydride) to a suspension of (S)-(+)-10,11-dihydro-10-hydroxy-5H-dibenz/b,f/azepine-5-carboxamide (I) and pyridine in dichloromethane, as described in example 4 of U.S. Pat. No. 5,753,646.

The compounds described in examples 4 to 17 of U.S. Pat. No. 5,753,646 can be produced by acylation using the appropriate acyl chloride or anhydride. The compounds described in examples 18 to 23 can be produced using the appropriate carboxylic acid.

Using the present invention, it is therefore possible to produce the following compounds:

(1) 10-acetoxy-10,11-dihydro-5H-dibenz/b,f/azepine-5-carboxamide
(2) 10-benzoyloxy-10,11-dihydro-5H-dibenz/b,f/azepine-5-carboxamide
(3) 10-(4-methoxybenzoyloxy)-10,11-dihydro-5H-dibenz/b,f/azepine-5-carboxamide
(4) 10-(3-methoxybenzoyloxy)-10,11-dihydro-5H-dibenz/b,f/azepine-5-carboxamide
(5) 10-(2-methoxybenzoloxy)-10,11-dihydro-5H-dibenz/b,f/azepine-5-carboxamide
(6) 10-(4-nitrobenzoyloxy)-10,11-dihydro-5H-dibenz/b,f/azepine-5-carboxamide
(7) 10-(3-nitrobenzoyloxy)-10,11-dihydro-5H-dibenz/b,f/azepine-5-carboxamide
(8) 10-(2-nitrobenzoyloxy)-10,11-dihydro-5H-dibenz/b,f/azepine-5-carboxamide
(9) 10-(4-chlorobenzoyloxy)-10,11-dihydro-5H-dibenz/b,f/azepine-5-carboxamide
(10) 10-(3-chlorobenzoyloxy)-10,11-dihydro-5H-dibenz/b,f/azepine-5-carboxamide
(11) 10-(2-acetoxybenzoyloxy)-10,11-dihydro-5H-dibenz/b,f/azepine-5-carboxamide
(12) 10-propionyloxy-10,11-dihydro-5H-dibenz/b,f/azepine-5-carboxamide
(13) 10-butyryloxy-10,11-dihydro-5H-dibenz/b,f/azepine-5-carboxamide
(14) 10-pivaloyloxy-10,11-dihydro-5H-dibenz/b,f/azepine-5-carboxamide
(15) 10-[(2-propyl)pentanoyloxy]-10,11-dihydro-5H-dibenz/b,f/azepine-5-carboxamide
(16) 10-[(2-ethyl)hexanoyloxy]-10,11-dihydro-5H-dibenz/b,f/azepine-5-carboxamide
(17) 10-stearoyloxy-10,11-dihydro-5H-dibenz/b,f/azepine-5-carboxamide
(18) 10-cyclopentanoyloxy-10,11-dihydro-5H-dibenz/b,f/azepine-5-carboxamide
(19) 10-cyclohexanoyloxy-10,11-dihydro-5H-dibenz/b,f/azepine-5-carboxamide
(20) 10-phenylacetoxy-10,11-dihydro-5H-bibenz/b,f/azepine-5-carboxamide
(21) 10-(4-methoxyphenyl)acetoxy-10,11-dihydro-5H-dibenz/b,f/-azepine-5-carboxamide
(22) 10-(3-methoxyphenyl)acetoxy-10,11-dihydro-5H-dibenz/b,f/azepine-5-carboxamide
(23) 10-(4-nitrophenyl)acetoxy-10,11-dihydro-5H-dibenz/b,f/azepine-5-carboxamide
(24) 10-(3-nitrophenyl)acetoxy-10,11-dihydro-5H-dibenz/b,f/azepine-5-carboxamide
(25) 10-nicotinoyloxy-10,11-dihydro-5H-dibenz/b,f/azepine-5-carboxamide
(26) 10-isonicotinoyloxy-10,11-dihydro-5H-dibenz/b,f/azepine-5-carboxamide
(27) 10-chloroacetoxy-10,11-dihydro-5H-dibenz/b,f/azepine-5-carboxamide
(28) 10-bromoacetoxy-10,11-dihydro-5H-dibenz/b,f/azepine-5-carboxamide
(29) 10-formyloxy-10,11-dihydro-5H-dibenz/b,f/azepine-5-carboxamide
(30) 10-ethoxycarbonyloxy-10,11-dihydro-5H-dibenz/b,f/azepine-5-carboxamide
(31) 10-(2-chloropropionyloxy)-10,11-dihydro-5H-dibenz/b,f/azepine-5-carboxamide As already mentioned, the recovered racemic (±)-10,11-dihydro-10-hydroxy-5H-dibenz/b,f/azepine-5-carboxamide (III) may be resolved into its optically pure (R)-(+)- and (S)-(−)-stereoisomers (II) and (I), whereby the desired (R)-(+)- or (S)-(−)-stereoisomers of all of the above compounds may be produced.

These compounds, or pharmaceutically acceptable derivatives thereof (such as salts), can be used in the preparation of pharmaceutical compositions comprising the compound itself, or the derivative, in combination with a pharmaceutically acceptable carrier. Such compositions have anticonvulsant properties and can be used in the treatment of some central and peripheral nervous system disorders, such as epilepsy.

EXAMPLES

The invention disclosed herein is exemplified by the following examples of preparation. It is to be understood that the invention is not to be limited to the exact details of operation, as obvious modifications and equivalents will be apparent to those skilled in the art.

Example 1

To a stirred suspension of (R)-(−)-10,11-dihydro-10-hydroxy-5H-dibenz/b,f/azepine-5-carboxamide (II) (100 g, 393.7 mmol) (98.67% optical purity by chiral HPLC analysis) in dichloromethane (1000 mL) cooled to 0–5° C. was added thionyl chloride (56.2 g, 472.4 mmol) dropwise. The reaction mixture, which became a solution towards the end of addition, was allowed to stir for a further 10 minutes. A small quantity of activated charcoal was added with stirring and the reaction mixture was then filtered through a short Celite pad. The filtrate was then evaporated (40° C., water-aspirator pressure) to a small residual volume. Toluene (500 mL) was added, and the mixture was again evaporated (40° C., water-aspirator pressure) to leave a solid. Ethyl acetate (300 mL) was added and the slurry was stirred at room temperature for one hour, whereupon the solid was removed by filtration and washed by a small volume of cold ethyl acetate. After drying to constant weight, there was obtained 10-chloro-10,11-dihydro-5H-dibenz/b,f/azepine-5-carboxamide (VII) as a beige solid (97.48 g, 91%) of m.p. 156–157° C.

Example 2

To a stirred suspension of (R)-(−)-10,11-dihydro-10-hydroxy-5H-dibenz/b,f/azepine-5-carboxamide (II) (4.29 g, 16.89 mmol) (99.2% optical purity by chiral HPLC analysis) in dichloromethane (50 mL) cooled to 0–5° C. was added thionyl chloride (2.22 g, 18.58 mmol) dropwise. The reaction mixture, which became a solution towards the end of addition, was allowed to stir for a further 10 minutes, whereupon ice/water was added. The phases were separated and the aqueous phase was extracted with a small volume of dichloromethane. The combined organic layers were washed by water and brine, then dried over anhydrous magnesium sulphate, filtered and evaporated (40° C., water-aspirator pressure) to leave a white solid. Ethyl acetate (20 mL) was added and the slurry was stirred at room temperature for one hour. The solid was removed by filtration and dried until constant weight to afford 10-chloro-10,11-dihydro-5H-dibenz/b,f/azepine-5-carboxamide (VII) as a white solid (4.22 g, 92%) of m.p. 156.3–156.6° C.

Example 3

A suspension of 10-chloro-10,11-dihydro-5H-dibenz/b,f/azepine-5-carboxamide (VII) (50.0 g, 183.5 mmol) in de-ionised water (900 mL) was stirred at room temperature for forty-eight hours. The solid was removed by filtration and washed with de-ionised water (100 mL). After drying at 50° C. over phosphorus pentoxide under high vacuum until constant weight, there was obtained racemic (±)-10,11-dihydro-10-hydroxy-5H-dibenz/b,f/azepine-5-carboxamide (III) as a beige solid (42.12 g, 90%), of m.p. 186–188° C.

Chiral HPLC analysis of this product (LiChroCART 250-4 HPLC Cartridge ChiraDex 5 μm, (Merck), Flowrate: 0.8 mL/min, Mobile Phase: water/methanol 8:2, sample injected was 20 μL of 0.2 mg analyte/mL dissolved in the mobile phase, and UV detection at 210/254 nm showed complete racemisation (1:1 mixture of (S)-(+)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II), with retention time of (R)-(−)-10,11-dihydro-10-hydroxy-5H-dibenz/b,f/azepine-5-carboxamide (II) at 8.39 minutes and retention time of (S)-(+)-10,11-dihydro-10-hydroxy-5H-dibenz/b,f/azepine-5-carboxamide (1) at 9.1 minutes).

Example 4

A stirred suspension of 10-chloro-10,11-dihydro-5H-dibenz/b,f/azepine-5-carboxamide (VII) (7.68 g, 28.16 mmol) in a mixture of dioxane (40 mL) and water (40 mL) was stirred at 50° C. for forty minutes. The organic solvent was then removed by evaporation (40° C., water-aspirator pressure) and water (40 mL) was added to the residue, which was then extracted with a 10% isopropanol/dichloromethane solvent mixture. The combined organic extracts were washed with water and brine, then dried over anhydrous magnesium sulphate, filtered and evaporated (40° C., water-aspirator pressure) to leave a pale yellowish foam. Recrystallisation from a dichloromethane/isopropanol mixture afforded racemic (±)-10,11-dihydro-10-hydroxy-5H-dibenz/b,f/azepine-5-carboxamide (III) as white crystals (4.92 g, 69%), of m.p. 186.5–188° C.

Chiral HPLC analysis of this product (LiChroCART 250-4 HPLC Cartridge ChiraDex 5 μm, (Merck), Flowrate: 0.8 mL/min, Mobile Phase: water/methanol 8:2, sample injected was 20 μL of 0.2 mg analyte/mL dissolved in the mobile phase, and UV detection at 210/254 nm showed complete racemisation (1:1 mixture of (S)-(+)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II), with retention time of (R)-(−)-10,11-dihydro-10-hydroxy-5H-dibenz/b,f/azepine-5-carboxamide (II) at 8.39 minutes and retention time of (S)-(+)-10,11-dihydro-10-hydroxy-5H-dibenz/b,f/azepine-5-carboxamide (1) at 9.1 minutes).

Example 5

To a stirred suspension of (S)-(+)-10,11-dihydro-10-hydroxy-5H-dibenz/b,f/azepine-5-carboxamide (II) (10 g, 39.37 mmol) (87% optical purity by chiral HPLC analysis) in dichloromethane (100 mL) cooled to 0–5° C. was added thionyl chloride (5.62 g, 47.24 mmol) dropwise. The reaction mixture, which became a solution towards the end of addition, was allowed to stir for a further 10 minutes, whereupon ice/water was added. The phases were separated and the aqueous phase was extracted with a small volume of dichloromethane. The combined organic layers were washed by water and brine, then dried over anhydrous magnesium sulphate, then filtered and evaporated (40° C., water-aspirator pressure) to leave a white solid. Ethyl acetate (50 mL) was added and the slurry was stirred at room temperature for one hour. The solid was removed by filtration and dried until constant weight to afford 10-chloro-10,11-dihydro-5H-dibenz/b,f/azepine-5-carboxamide (VII) as a white solid (9.98 g, 93%) of m.p. 155–157° C.

This intermediate was hydrolysed as described in Example 3 to give the perfectly racemic product (±) 10,11-dihydro-10-hydroxy-5H-dibenz/b,f/azepine-5-carboxamide (III) as judged by chiral HPLC analysis It will be appreciated that the invention described above may be modified.

What is claimed is:

1. 10-chloro-10,11-dihydro-5H-dibenz[b,f]azepine-5-carboxamide (VII)

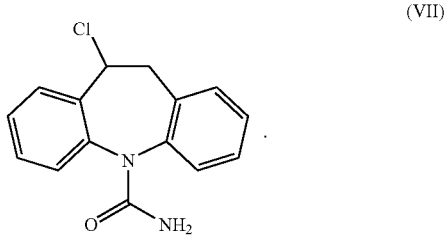

(VII)

2. A method for the manufacture of the compound (VII) as defined in claim 1, comprising reacting optically pure or optically enriched (R)-(−)-10,11-dihydro-10-hydroxy-5H-dibenz[b,f]azepine-5-carboxamide (II), or reacting optically pure or optically enriched (S)-(+)-10,11-dihydro-10-hydroxy-5H-dibenz[b,f]azepine-5-carboxamide (I), with a chlorinating reagent in a substantially inert solvent to give the compound of formula (VII).

3. A method according to claim 2, wherein the chlorinating reagent is chosen from thionyl chloride, oxalyl chloride, sulfuryl chloride, phosphorus pentachloride, phosphorus trichloride or phosphorus oxychloride.

4. A method according to claim 2, wherein the substantially inert solvent is a chlorinated aliphatic or aromatic hydrocarbon solvent.

5. A method according to claim 2, wherein hydrolysis of the intermediate (VII) is carried out in neat water.

6. A method according to claim 2, wherein hydrolysis of the intermediate (VII) is carried out in a water/water-miscible solvent mixture.

7. A method according to claim 6, wherein the water-miscible solvent is chosen from dioxane, tetrahydrofuran, methanol, ethanol, isopropanol, N-methyl-2-pyrrolidinone, high molecular weight polyethyleneglycols, acetone, acetonitrile and dimethylformamide.

8. A method for the racemisation of optically pure or optically enriched (R)-(−)-10,11-dihydro-10-hydroxy-5H-dibenz[b,f]azepine-5-carboxamide (II) comprising:
(a) reacting optically pure or optically enriched (R)-(−)-10,11-dihydro-10-hydroxy-5H-dibenz[b,f]azepine-5-carboxamide (II) with a chlorinating reagent in a substantially inert solvent to give the intermediate of formula (VII), and
(b) hydrolysing the resulting intermediate of formula (VII) to give racemic (±)-10,11-dihydro-10-hydroxy-5H-dibenz[b,f]azepine-5-carboxamide (III).

9. A method according to claim 8, wherein the chlorinating reagent is chosen from thionyl chloride, oxalyl chloride, sulfuryl chloride, phosphorus pentachloride, phosphorus trichloride or phosphorus oxychloride.

10. A method according to claim 8, wherein the substantially inert solvent is a chlorinated aliphatic or aromatic hydrocarbon solvent.

11. A method according to claim 8, wherein hydrolysis of the intermediate (VII) is carried out in neat water.

12. A method according to claim 8, wherein hydrolysis of the intermediate (VII) is carried out in a water/water-miscible solvent mixture.

13. A method according to claim 12, wherein the water-miscible solvent is chosen from dioxane, tetrahydrofuran, methanol, ethanol, isopropanol, N-methyl-2-pyrrolidinone, high molecular weight polyethyleneglycols, acetone, acetonitrile and dimethylformamide.

14. A method for the racemisation of optically pure or optically enriched (S)-(+)-10,11-dihydro-10-hydroxy-5H-dibenz[b,f]azepine-5-carboxamide (I) comprising:
(a) reacting optically pure or optically enriched (S)-(+)-10,11-dihydro-10-hydroxy-5H-dibenz[b,f]azepine-5-carboxamide (I) with a chlorinating reagent in a substantially inert solvent to give the intermediate of formula (VII), and
(b) hydrolysing the resulting intermediate of formula (VII) to give racemic (±)-10,11-dihydro-10-hydroxy-5H-dibenz[b,f]azepine-5-carboxamide (III).

15. A method according to claim 14, wherein the chlorinating reagent is chosen from thionyl chloride, oxalyl chloride, sulfuryl chloride, phosphorus pentachloride, phosphorus trichloride or phosphorus oxychloride.

16. A method according to claim 14, wherein the substantially inert solvent is a chlorinated aliphatic or aromatic hydrocarbon solvent.

17. A method according to claim 14, wherein hydrolysis of the intermediate (VII) is carried out in neat water.

18. A method according to claim 14, wherein hydrolysis of the intermediate (VII) is carried out in a water/water-miscible solvent mixture.

19. A method according to claim 18, wherein the water-miscible solvent is chosen from dioxane, tetrahydrofuran, methanol, ethanol, isopropanol, N-methyl-2-pyrrolidinone, high molecular weight polyethyleneglycols, acetone, acetonitrile and dimethylformamide.

20. A method for the preparation of a compound of general formula (VIII):

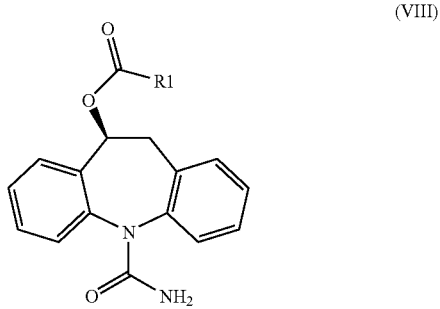

(VIII)

where R1 is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising:

(a) forming racemic (±)-10,11-dihydro-10-hydroxy-5H-dibenz[b,f]azepine-5-carboxamide from optically pure or optically enriched (R)-(−)-10,11-dihydro-10-hydroxy-5H-dibenz[b,f]azepine-5-carboxamide (II) by
  (i) reacting optically pure or optically enriched (R)-(−)-10,11-dihydro-10-hydroxy-5H-dibenz[b,f]azepine-5-carboxamide (II) with a chlorinating reagent in a substantially inert solvent to give the intermediate of formula (VII), and
  (ii) hydrolysing the resulting intermediate of formula (VII) to give racemic (±)-10,11-dihydro-10-hydroxy-5H-dibenz[b,f]azepine-5-carboxamide (III), then, after step (a):
(b) treating the racemic (±)-10,11-dihydro-10-hydroxy-5H-dibenz[b,f]azepine-5-carboxamide to produce the compound of formula (VIII).

21. A method according to claim 20, wherein the treatment of the racemic (±)-10,11-dihydro-10-hydroxy-5H-dibenz[b,f]azepine-5-carboxamide involves a resolution step to isolate (S)-(+)-10,11-dihydro-10-hydroxy-5H-dibenz[b,f]azepine-5-carboxamide (I), followed by acylation of the isolated enantiomer to produce the compound of formula (VIII).

22. A method according to claim 21, wherein the acylation step is effected in dichloromethane in the presence of pyridine.

23. A method for the preparation of a compound of general formula (VIII):

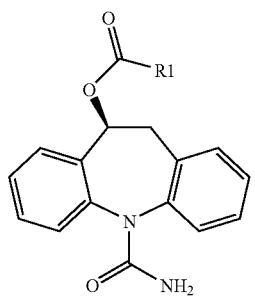

(VIII)

where R1 is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising:

(a) forming racemic (±)-10,11-dihydro-10-hydroxy-5H-dibenz[b,f]azepine-5-carboxamide from optically pure or optically enriched (S)-(+)-10,11-dihydro-10-hydroxy-5H-dibenz[b,f]azepine-5-carboxamide (I) by
  (i) reacting optically pure or optically enriched (S)-(+)-10,11-dihydro-10-hydroxy-5H-dibenz[b,f]azepine-5-carboxamide (I) with a chlorinating reagent in a substantially inert solvent to give the intermediate of formula (VII), and
  (ii) hydrolysing the resulting intermediate of formula (VII) to give racemic (±)-10,11-dihydro-10-hydroxy-5H-dibenz[b,f]azepine-5-carboxamide (III), then, after step (a):
(b) treating the racemic (±)-10,11-dihydro-10-hydroxy-5H-dibenz[b,f]azepine-5-carboxamide to produce the compound of formula (VIII).

24. A method according to claim 23, wherein the treatment of the racemic (±)-10,11-dihydro-10-hydroxy-5H-dibenz[b,f]azepine-5-carboxamide involves a resolution step to isolate (S)-(+)-10,11-dihydro-10-hydroxy-5H-dibenz[b,f]azepine-5-carboxamide (I), followed by acylation of the isolated enantiomer to produce the compound of formula (VIII).

25. A method according to claim 24, wherein the acylation step is effected in dichloromethane in the presence of pyridine.

26. A method for the preparation of a compound of general formula (IX):

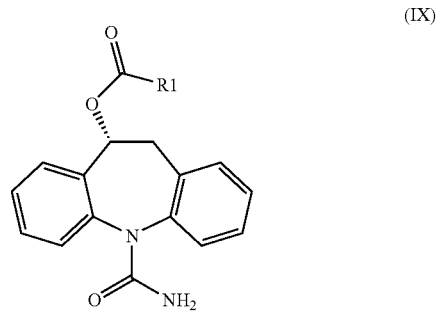

(IX)

where R1 is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising:

(a) forming racemic (±)-10,11-dihydro-10-hydroxy-5H-dibenz[b,f]azepine-5-carboxamide from optically pure or optically enriched (R)-(−)-10,11-dihydro-10-hydroxy-5H-dibenz[b,f]azepine-5-carboxamide (II) by
  (i) reacting optically pure or optically enriched (R)-(−)-10,11-dihydro-10-hydroxy-5H-dibenz[b,f]azepine-5-carboxamide (II) with a chlorinating reagent in a substantially inert solvent to give the intermediate of formula (VII), and
  (ii) hydrolysing the resulting intermediate of formula (VII) to give racemic (±)-10,11-dihydro-10-hydroxy-5H-dibenz[b,f]azepine-5-carboxamide (III), then, after step (a):
(b) treating the racemic (±)-10,11-dihydro-10-hydroxy-5H-dibenz[b,f]azepine-5-carboxamide to produce the compound of formula (IX).

27. A method according to claim 26, wherein the treatment of the racemic (±)-10,11-dihydro-10-hydroxy-5H-dibenz[b,f]azepine-5-carboxamide involves a resolution step to isolate (R)-(−)-10,11-dihydro-10-hydroxy-5H-dibenz[b,f]azepine-5-carboxamide (II), followed by acylation of the isolated enantiomer to produce the compound of formula (IX).

28. A method according to claim 27, wherein the acylation step is effected in dichloromethane in the presence of pyridine.

29. A method for the preparation of a compound of general formula (IX):

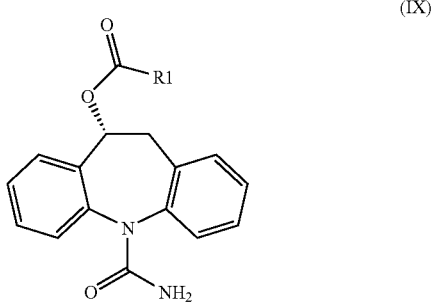

(IX)

where R1 is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising:

(a) forming racemic (±)-10,11-dihydro-10-hydroxy-5H-dibenz[b,f]azepine-5-carboxamide from optically pure or optically enriched (S)-(+)-10,11-dihydro-10-hydroxy-5H-dibenz[b,f]azepine-5-carboxamide by (i) reacting optically pure or optically enriched (S)-(+)-10,11-dihydro-10-hydroxy-5H-dibenz[b,f]azepine-5-carboxamide (I) with a chlorinating reagent in a substantially inert solvent to give the intermediate of formula (VII), and (ii) hydrolysing the resulting intermediate of formula (VII) to give racemic (±)-10,11-dihydro-10-hydroxy-5H-dibenz[b,f]azepine-5-carboxamide (III), then, after step (a):

(b) treating the racemic (±)-10,11-dihydro-10-hydroxy-5H-dibenz[b,f]azepine-5-carboxamide to produce the compound of formula (IX).

30. A method according to claim 29, wherein the treatment of the racemic (±)-10,11-dihydro-10-hydroxy-5H-dibenz[b,f]azepine-5-carboxamide involves a resolution step to isolate (R)-(−)-10,11-dihydro-10-hydroxy-5H-dibenz[b,f]azepine-5-carboxamide (II), followed by acylation of the isolated enantiomer to produce the compound of formula (IX).

31. A method according to claim 30, wherein the acylation step is effected in dichloromethane in the presence of pyridine.

32. A method for the preparation of (S)-(−)-10-acetoxy-10,11-dihydro-5H-dibenz[b,f]azepine-5-carboxamide (V) comprising forming racemic (±)-10,11-dihydro-10-hydroxy-5H-dibenz[b,f]azepine-5-carboxamide (III) from optically pure or optically enriched (R)-(−)-10,11-dihydro-10-hydroxy-5H-dibenz[b,f]azepine-5-carboxamide (II) by (i) reacting optically pure or optically enriched (R)-(−)-10,11-dihydro-10-hydroxy-5H-dibenz[b,f]azepine-5-carboxamide (II) with a chlorinating reagent in a substantially inert solvent to give the intermediate of formula (VII), and (ii) hydrolysing the resulting intermediate of formula (VII) to give racemic (±)-10,11-dihydro-10-hydroxy-5H-dibenz[b,f]azepine-5-carboxamide (III), then resolving and acylating the (S)-(+)-10,11-dihydro-10-hydroxy-5H-dibenz[b,f]azepine-5-carboxamide (I).

33. A method according to claim 32, wherein the acylation step is effected in dichloromethane in the presence of pyridine.

34. A method for the preparation of (R)-(+)-10-acetoxy-10,11-dihydro-5H-dibenz[b,f]azepine-5-carboxamide (VI) comprising forming racemic (±)-10,11-dihydro-10-hydroxy-5H-dibenz[b,f]azepine-5-carboxamide (III) from optically pure or optically enriched (S)-(+)-10,11-dihydro-10-hydroxy-5H-dibenz[b,f]azepine-5-carboxamide (I) by (i) reacting optically pure or optically enriched (S)-(+)-10,11-dihydro-10-hydroxy-5H-dibenz[b,f]azepine-5-carboxamide (I) with a chlorinating reagent in a substantially inert solvent to give the intermediate of formula (VII), and (ii) hydrolysing the resulting intermediate of formula (VII) to give racemic (±)-10,11-dihydro-10-hydroxy-5H-dibenz[b,f]azepine-5-carboxamide (III), then resolving and acylating the (R)-(−)-10,11-dihydro-10-hydroxy-5H-dibenz[b,f]azepine-5-carboxamide (II).

35. A method according to claim 34, wherein the acylation step is effected in dichloromethane in the presence of pyridine.

* * * * *

UNITED STATES PATENT AND TRADEMARK OFFICE
CERTIFICATE OF CORRECTION

PATENT NO. : 7,189,846 B2 Page 1 of 1
APPLICATION NO. : 10/842726
DATED : March 13, 2007
INVENTOR(S) : David Alexander Learmonth It is certified that error appears in the above-identified patent and that said Letters Patent is hereby corrected as shown below:

Title page, and Column 1,
Item 73, the Assignee should read --Portela & C.A., S.A., Mamede Do Coronado (PT)--

In Column 13, Lines 32 and 33 replace "(S)-(+)-10,11-dihydro-10-hydroxy-5H-dibenz[b,f]azepine-5-carboxamide" with --(S)-(+)-10,11-dihydro-10-hydroxy-5H-dibenz[b,f]azepine-5-carboxamide (I)--

Signed and Sealed this

Twenty-fourth Day of February, 2009

JOHN DOLL
*Acting Director of the United States Patent and Trademark Office*